Figure 1:
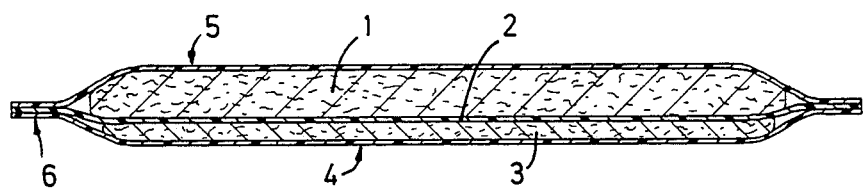

United States Patent [19]

Kamme

[11] Patent Number: 4,820,293
[45] Date of Patent: Apr. 11, 1989

[54] ABSORBENT BODY WITH SEMIPERMEABLE MEMBRANE

[76] Inventor: Carl G. Kamme, Bengt Lidforss väg 8, S-223 65 Lund, Sweden

[21] Appl. No.: 525,046

[22] PCT Filed: Nov. 25, 1982

[86] PCT No.: PCT/SE82/00397
§ 371 Date: Jul. 25, 1983
§ 102(e) Date: Jul. 25, 1983

[87] PCT Pub. No.: WO83/02054
PCT Pub. Date: Jun. 23, 1983

[30] Foreign Application Priority Data

Dec. 11, 1981 [SE] Sweden .................... 8107437

[51] Int. Cl.$^4$ .................................... A61F 13/16
[52] U.S. Cl. .................................... 604/368
[58] Field of Search ............... 128/155, 156; 604/368

[56] References Cited

U.S. PATENT DOCUMENTS

| | | | |
|---|---|---|---|
| 3,121,427 | 2/1964 | Mosier | 604/368 |
| 3,490,454 | 11/1970 | Goldfarb et al. | 604/368 |
| 4,055,180 | 10/1977 | Karami | 604/368 |
| 4,102,340 | 7/1978 | Mesek et al. | 604/368 |
| 4,456,570 | 6/1984 | Thomas et al. | 264/22 |

*Primary Examiner*—C. Fred Rosenbaum
*Attorney, Agent, or Firm*—Cushman, Darby & Cushman

[57] ABSTRACT

Absorbent body consisting of a fluid-absorbing substance (1) which is enclosed in a jacket (2,5), and outside the jacket a fluid-absorbing layer (3), e.g. cellulose wadding, at least on the portion of the jacket intended to face the fluid-discharging region, and possibly outside this layer a wound-protecting layer (4), at least a portion (2) of the jacket, which is in contact with the absorbent layer (3), being made of a semipermeable membrane film which is permeable to the fluid discharged from the fluid-discharging region but which is not permeable to the fluid-absorbing substance, the remainder of said jacket (5) consisting of a liquid-tight material.

23 Claims, 1 Drawing Sheet

ABSORBENT BODY WITH SEMIPERMEABLE MEMBRANE

The present invention relates to an absorbent body which comprises an absorbent layer, a jacket and possibly a wound-protecting layer. The absorbent body can be used e.g. in compresses, various types of dressings and bandages and for collecting fluids from natural or artificial bodily openings.

The conventional and known materials used at present for collecting (absorbing) fluids from natural or artificial bodily openings, naturally occuring or artificial wounds, discharging skin and mucous membrane surfaces, are usually cotton or cellulose, possibly covered with a permeable layer such as perforated sheet or gauze designed to lie in contact with the fluid-discharging surface or the fluid-discharging region. The fluid is absorbed by the absorbent material by simple diffusion or by a certain amount of capillary force. The fluid-discharging region is therefore always in direct contact with the fluid collected in the absorbent material, which causes irritation of the tissues with harmful effect on healing and risk of subsequent infection. In the fluid collected in the absorbent material there is a massive growth of bacteria, which increases the risk of infection and spreading of infection in a hospital environment for example, and produces unpleasantness due to the foul-smelling products formed when bacteria grow in the presence of blood and blood serum.

The volume of secretion or fluid which a conventional compress of size 100×100 mm can abosrb from a wound, for example, is at most 15 ml. The compress is then dripping wet and in most cases grown-through with up to about $10^8$ bacteria per ml of fluid.

Many attempts have been made to overcome the disadvantages of the present dressings. Swedish Patent Specification No. 7205809-2 reveals a non-adherent layer, possibly with a germicidal agent. U.S. Pat. No. 3,446,208 also describes a non-adherent layer, as does U.S. Pat. No. 3,006,338 which describes a dressing with a non-adherent, perforated layer of gauze which has been treated with a film-forming material. U.S. Pat. No. 3,426,754 describes a dressing which is microporous to permit access to air to the wound. U.S. Pat. No. 3,113,568 describes a styptic bandage which comprises a net-like barrier for facilitating coagulation of blood.

Danish Patent Specification No. 138,972 describes an asorbent material containing fiber-coated hydrogel particles. Similar polymers which, upon absorption of water, form gels are described in Swedish Patent Specification No. 7013465-5 and in U.S. Pat. Nos. 3,419,006, 3,664,343, 3,783,872, 3,669,103 and 3,670,731. U.S. Pat. No. 3,883,256 describe an absorbent bandage containing a tight layer of absorbent particles which upon absorption of liquid expand and melt together into a gel. The layer then prevents the liquid absorbed into the bandage from being pressed out therefrom under pressure. U.S. Pat. No. 3,678,933 describes a bandage with several layers with an absorbent layer in the middle and on either side a "screen" of thermoplastic film pressed onto a scrim so that the plastic wraps itself around the fibers in the scrim forming holes through which the liquid can penetrate to the absorbent material.

None of the bandages in the above mentioned specifications contains a semipermeable membrane or uses osmotic pressure differentials and therefore they have no similarity to the present inventive principle.

The purpose of the present invention is to achieve an absorbent body which takes up a large amount of fluid, e.g. secretion, and permanently encloses the fluid.

These purposes are achieved according to the invention with an absorbent body which comprises an absorbent layer, a jacket and possibly a wound-protecting layer and which, according to the invention, is characterized in that it consists of a fluid-absorbing substance which is enclosed in the jacket. Outside the jacket there is a fluid-absorbing layer, e.g. cellulose wadding, at least on the portion of the jacket intended to face the fluid-discharging region. The absorbent body possibly comprises, even outside the fluid-absorbing layer, a wound-protecting layer. At least the portion of the jacket which is in contact with the absorbent layer is made of a semipermeable membrane film, which is permeable to the fluid discharged from the fluid-discharging region but which is not permeable to the fluid-absorbing substance. the rest of the jacket is liquid-tight.

In the present description and claims, "fluid-absorbing substance" refers to a substance which sucks up fluid and retains it with greater force than conventional absorbent material, e.g. cellulose wadding. This is achieved by the fuid-absorbing substance producing an osmotic pressure differential.

At constant fluid flow, the fluid is continuously removed from the fluid-discharging region. The fluid passes through the semipermeable membrane and is collected inside the absorbent body, and is thereafter no longer in contact with the fluid-discharging region, and therefore no tissue irritation occurs when using the absorbent body according to the invention. By virtue of the fact that the fluid is continuously removed and is enclosed in the absorbent body, the growth conditions for bacteria in the fluid-discharging region will be unfavourable. The fluid enclosed in the absorbent body is sterile, i.e. bacteria-free, if the pore size of the semipermeable membrane is less than 1 $\mu$m. If the pore size of the semipermeable membrane is larger, bacteria will also be enclosed in the absorbent body. In both cases, the top of the jacket or bandage will not be contaminated by bacteria coming from below. Therefore there will be no spreading of infection from the dressing to the surroundings.

If there is rapid discharge of fluid from natural or artificial bodily openings for example, the absorbent body cannot absorb all fluid immediately; rather it should first be absorbed by conventional absorbent material and then be transported into the absorbent body.

If there is intermittent discharge, the fluid discharging region will be dry as soon as the fluid has been taken up by the absorbent body, thereby avoiding tissue irritation and secondary infection.

The volume of secretion or fluid which an absorbent body of size 100×100 mm can absorb from a wound, for example, is at least 80 ml.

The fluid-absorbing substance in the absorbent body must have a molecular weight which is large enough so that the substance cannot pass through the pores of the semipermeable membrane. If a liquid substance is used or a substance which becomes liquid upon absorption of fluid, the osmotic pressure differential between the inside and the outside of the membrane will drive the fluid into the absorbent body and retain it there. If the fluid-absorbing substance is not soluble in fluid, the fluid-absorbing capacity of the substance is dependent on the capacity of the substance to bind the fluid. It is also possible to use a mixture of a fluid-absorbing substance, which provides an osmotic effect, e.g. polyethylene glycol, and a solid gel-forming liquid-absorbing substance, e.g. a carboxy-methylated cellulose derivative. Examples of fluid-absorbing substances are polyvinyl pyrrolidone, polymers of sugars such as saccharose, polyethylene glycol, branched polymers of starch, carboxy-methylated cellulose derivatives of cross-linked type and modified hydrophilic polyacrylates.

Preferably substances with a high fluid absorption capacity per unit of weight are used, such as polyethylene glycol with a molecular weight of, for example, 500-80,000, suitably 1,500-20,000 and especially about 20,000 branched polymers of starch, e.g. polymer 35-A-100, carboxymethylated cellulose derivative of cross-linked type, e.g. Aqualon ® or hydrophilic polyacrylates, e.g. Permasorb.

The semipermeable membrane can consist of cellulose, regenerated cellulose, cellulose nitrate, cellulose acetate, cellulose acetate-butyrate, polycarbonate, polyamide, fiberglass, polysulfone, or polytetrafluoroethylene, e.g. PTFE "Sartorius". A suitable pore size for said materials is 0.001 µm—20 µm, preferably 0.005—8 µm, especially about 0.01 µm. If the membrane is made of cellulose, the mechanical strength can be increased by impregnating the membrane with a solution containing polyacrylates. The membrane can also consist of polyacrylate film with hydrophilic groups, e.g. carboxyl groups. The polyacrylate film can be placed on a carrier of non-woven or spun-bonded material for example with an area weight of 20-50 g per m². The membrane can also be made of cellophane with a polymerization number of 300-500, suitably 400-500, preferably of dialysis quality.

Figure 2:
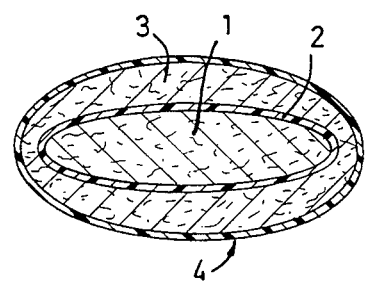

The invention will be described in the following with reference to the accompanying drawing, in which FIG. 1 shows a section through an absorbent body according to the invention, and FIG. 2 shows a section through another embodiment of an absorbent body according to the invention.

FIG. 1 shows an embodiment of the present absorbent body. It consists of a fluid-absorbing substance 1, which is enclosed in a jacket consisting of a tight backing material, e.g. a polyethylene film 5 fused to a semipermeable layer 2. Beneath the semipermeable layer there is an absorbent material 3, e.g. fluff. Beneath the layer of absorbent material there is a non-adherent layer 4.

FIG. 2 shows another embodiment of the invention, in which the fluid-absorbing substance 1 is completely enclosed by a semipermeable membrane 2. The semipermeable membrane is surrounded on all sides by an absorbent layer 3 which is in turn enveloped by a non-adherent layer 4. In this embodiment of the invention, fluid is absorbed through both sides of the absorbent body.

A few examples will be given below, which show different membrane materials and fluid-absorbing materials. In the examples the following abbreviations are used: PEG=polyethylene glycol, Mw=molecular weight, PVP=polyvinyl pyrrolidone.

UPTAKE OF LIQUID IN ABSORBENT BODY (CONTAINER) WITH SEMI-PERMEABLE MEMBRANE

Method: The bag is provided with a layer of thin gauze on the side through which the liquid is absorbed. The bag is placed in a petri dish with liquid. Tap water with 3.5% polyvinyl pyrrolidone Mw 40,000 (PVP-40), produces an osmotic pressure of 400 mm of water corresponding to the colloid-osmotic pressure of serum.

Example I

Liquid: Tap water with 3.5% PVP-40, supplied in excess. Membrane: cellophane of dialysis quality, pore size 0.001 µm. Membrane surface: 7×9 cm.

| Fluid-absorbing substance | Absorbed volume (ml) after | | |
|---|---|---|---|
| ca 2.5 g/container | 2 h | 24 h | 48 h |
| PEG Mw 20,000 | 16 | 34 | 35 |
| PEG Mw 6,000 | 21 | 32 | 32 |
| PEG Mw 4,000 | 26 | 34 | 33 |
| PEG Mw 1,500 | 28 | 32 | 34 |
| Polymer of glucose (Dextran) | 6 | 9 | 9 |
| PVP Mw 40,000 | 10 | 12 | 12 |
| "Permasorb 30" + PEG Mw 20,000 | 30 | 34 | 35 |
| "Polymer 35-A-100" + PEG Mw 20,000 | 31 | 34 | 36 |

Example II

Liquid: Tap water with 3.5% PVP-40, supplied in excess. Membrane: thin cellophane not of dialysis quality. Membrane surface: 7×8 cm.

| Fluid-absorbing substance | Absorbed volume (ml) after | | |
|---|---|---|---|
| 2 g/container | 2 h | 24 h | 48 h |
| PEG Mw 20,000 | 18 | 32 | 32 |
| PEG Mw 6,000 | 20 | 0 | 0 |
| PEG Mw 4,000 | 21 | 0 | 0 |
| PEG Mw 1,500 | 24 | 0 | 0 |
| Polymer of glucose (Dextran) | 9 | 9 | 8 |
| PVP Mw 40,000 | 11 | 10 | 11 |
| "Permasorb 30" + PEG Mw 20,000 | 29 | 31 | 31 |
| "Polymer 35-A-100" + PEG Mw 20,000 | 32 | 33 | 33 |

Example III

Liquid: Tap water with 3.5% PVP-40, supplied in excess. Membrane: cellulose nitrate, pore size 0.01 µm. Membrane surface: 7×8 cm.

| Fluid-absorbing substance | Absorbed volume (ml) after | | |
|---|---|---|---|
| ca 2 g/container | 2 h | 24 h | 48 h |
| PEG Mw 20,000 | 25 | 33 | 34 |
| PEG Mw 6,000 | 28 | 0 | 0 |
| PEG Mw 4,000 | 29 | 0 | 0 |
| Polymer of glucose (Dextran) | 10 | 9 | 9 |
| PVP Mw 40,000 | 8 | 10 | 9 |
| "Permasorb 30" + PEG Mw 20,000 | 30 | 32 | 34 |
| "Polymer 35-A-100" + PEG Mw 20,000 | 31 | 34 | 35 |

Example IV

Liquid: Tap water with 3.5% PVP-40, supplied in excess. Membrane: cellulose nitrate, pore size 0.2 µm. Membrane surface: 7×8 cm.

| Fluid-absorbing substance | Absorbed volume (ml) after | | |
|---|---|---|---|
| ca 2 g/container | 2 h | 24 h | 48 h |
| PEG Mw 20,000 | 25 | 0 | 0 |
| PEG Mw 6,000 | 24 | 0 | 0 |
| Polymer of glucose (Dextran) | 8 | 6 | 6 |
| PVP Mw 40,000 | 9 | 8 | 8 |

-continued

| Fluid-absorbing substance ca 2 g/container | Absorbed volume (ml) after | | |
|---|---|---|---|
| | 2 h | 24 h | 48 h |
| "Permasorb 30" | 24 | 30 | 32 |
| "Polymer 35-A-100" | 26 | 32 | 34 |

As is evident from the above examples, different fluid-absorbing substances require different pore sizes. Pore size 0.001 μm retains PEG which is dissolved in the absorbed fluid, down to a molecular weight of 1,500. At pore size 0.01 μm PEG is retained with molecular weight 20,000 and at pore size 0.2 μm even this leaks out. "Permasorb" and Polymer 35-A-100 which do not provide any osmotic effect, require on the other hand larger pore size. When an absorbent body with a fluid absorbing substance which provides osmotic effect is used, a pore size <0.5 μm, especially ca 0.01 μm, is preferred.

Example V

Clinical study. Patient material: a patient with leg wound ca 100×250 mm on both sides of the left lower leg. Material: compresses with layers closest to the wound surface of conventional absorbent material. Container with membrane of cellulose nitrate, pore size 0.01 μm and with PEG Mw 20,000. The size of the compresses varied from 50×70 to 80×120 mm. The amount of PEG per container was 1.5-3 g. Conventional compresses were placed on one side, on the other compresses according to the invention. They were changed every other day. The result was registered at every change. Even at the first change, the wound had improved markedly on the side where the compresses according to the invention had been placed. After four changes the wound on that side was clean, with fresh granulation tissue and ingrowth of normal skin, while the wound which had been treated with conventional compresses was worse. The container of the compresses used contained 2-12 ml liquid.

Example VI

A flat bag of size about 50×50 mm is made of dialysis cellophane film. After filling with 10 g polyethylene glycol in powder form with molecular weight 1,500, the bag is closed so that it is entirely sealed. The bag is then placed in the centre of a self-adhesive tape material about 10×10 cm in size. Over the bag, an about 7×7 cm compress of gauze or similar absorbent material is placed on top of the bag, so that the extending edges of the compress can be pressed onto the tape material. To prevent adhesion to the wound, the sureface of the compress, which is to be in contact with the wound, is provided with a layer of permeable synthetic material, e.g. Monsanto's spun-bonded polyamide material "Cerex". Finally the entire surface is covered with a suitably divided siliconized protective paper. After sterilization with γ-radiation of ethylene oxide, the dressing is ready to be used for a heavily discharging leg wound, for example.

Example VII

A film-forming polyacrylate dispersion with hydrophilic groups in the form of carboxyl groups, e.g. Röhm's "Plextol 4871D", is mixed with another film-forming acrylate dispersion which produces a fusable film, e.g. Röhm's "Plextol B500", and an acrylate dispersion which in mixture with the others provide a non-sticking and non-blocking film, e.g. Röhm's "Plextol DV580". A suitable mixture can consist of 20% "Plextol 4871D", 60% "Plextol B500" and 20% "Plextol DV580", computed as dry substance.

The mixture obtained is cast on a film-casting paper into a transparent, elastic film which can be fused into the same type of bags as in Example VII. Dressings are made in the manner described in Example VII. The thickness of the cast film should be in the range of 50-100 μm and be adapted to the desired size and use of the finished dressing.

In the same manner, a vinyl acetate-acrylate copolymer with hydrophilic groups in the form of N-methylol groups, e.g. Wacker-Chemie's dispersion "Vinnapas LL420/5", is mixed with a polyvinyl acetate-polyethylene dispersion, which produces a fusable film, e.g. Wacker-Chemie's "Vinnapas EP1".

The mixture should contain about 50% of each component, computed as dry substance. In this case as well, the mixture obtained is cast into film. The thickness of the film should be in the range of 50-100 μm, and dressings can be made as in Example VII.

I claim:

1. An absorbent body for absorbing a fluid from a fluid-discharging region, comprising:
   an absorbent layer adapted to absorb said fluid;
   a jacket which is positioned immediately to contact with said absorbent layer, at least a portion of the jacket which is facing said absorbent layer been made of a micro-porous semi-permeable membrane film, which is permeable to said fluid discharged from said fluid-discharging region and absorbed by said absorbent layer, the remainder of said jacket being made of a liquid-tight material;
   a fluid absorbent substance causing osmotic activity being enclosed in said jacket and adapted to absorb said fluid, said membrane film being non-permeable to said fluid-absorbing substance;
   said semi-permeable membrane being liquid-tight when the osmotic pressure differential across said membrane is zero and being permeable to said fluid due to an osmotic pressure differential across said membrane.

2. An absorbent body according to claim 1, further comprising a wound-protecting layer provided outside said absorbent layer.

3. An absorbent body according to claim 1, wherein said fluid-absorbing substance is a substance which is solid and turns to liquid upon absorption of fluid.

4. An absorbent body according to claim 1, wherein said fluid-absorbing subtance is a liquid.

5. An absorbent body according to claim 1, wherein the fluid-absorbing substance comprises polyethylene glycol with a molecular weight of 500 to 80,000.

6. An absorbent body according to claim 5, wherein the polyethylene glycol has a molecular weight of about 1500 to 20,000.

7. An absorbent body according to claim 6, wherein the polyethylene glycol has a molecular weight of about 20,000.

8. An absorbent body according to claim 1, wherein the fluid-absorbing substance comprises a polymer of a sugar with a molecular weight of 10,000 to 400,000.

9. An absorbent body according to claim 8, wherein the polymer is a polymer of glucose.

10. An absorbent body according to claim 9, wherein the polymer is a dextran having a molecular weight of about 70,000.

11. An absorbent body according to claim 1, wherein the fluid-absorbing substance comprises 5 to 50 percent by weight of polyethylene glycol with a molecular weight of 500 to 80,000 or a polymer of a sugar with a molecular weight of 10,000 to 400,000.

12. An absorbent body according to claim 1, wherein the semi-permeable membrane has a pore size of 0.001–0.5 micrometer.

13. An absorbent body according to claim 12, wherein the semi-permeable membrane has a pore size of 0.001–0.01 micrometer.

14. An absorbent body according to claim 13, wherein the semi-permeable membrane has a pore size of about 0.01 micrometer.

15. An absorbent body according to claim 12, wherein the semi-permeable membrane consists of cellulose nitrate or cellulose acetate.

16. An absorbent body according to claim 12, wherein the semi-permeable membrane consists of cellulose acetate butyrate, a polycarbonate, a polyamide, or a polysulphon.

17. An absorbent body according to claim 12, wherein the semi-permeable membrane consists essentially of fibre glass, polytetrafluoroethylene, cellulose, or regenerated cellulose.

18. An absorbent body according to claim 17, wherein the cellulose membrane is mechanically reinforced by impregnation with polyacrylate.

19. An absorbant body according to claim 12, wherein the semi-permeable membrane consists of cellophane with a polymerization number of 300–500.

20. An absorbent body according to claim 12, wherein the semi-permeable membrane is a plastic film.

21. An absorbent body according to claim 20, wherein the plastic film is an acrylated film with hydrophilic groups, a copolymer of vinylacetateacrylate containing hydrophilic groups or a copolymer of ethylene-vinyl acetate containing hydrophilic groups.

22. An absorbent body according to claim 20, wherein the plastic film is provided with a fibre reinforcement.

23. An absorbent body according to claim 21, wherein the fibre-reinforcements is spun-bonded or non-woven material with an area weight of 20 to 50 $g/cm^2$.

* * * * *